US007479110B2

(12) United States Patent
Nishigaki et al.

(10) Patent No.: US 7,479,110 B2
(45) Date of Patent: Jan. 20, 2009

(54) ULTRASONIC DIAGNOSTIC EQUIPMENT

(75) Inventors: Morio Nishigaki, Fujisawa (JP); Takao Suzuki, Yokohama (JP)

(73) Assignee: Panasonic Corporation, Osaka (JP)

( * ) Notice: Subject to any disclaimer, the term of this patent is extended or adjusted under 35 U.S.C. 154(b) by 473 days.

(21) Appl. No.: 10/512,308

(22) PCT Filed: Apr. 18, 2003

(86) PCT No.: PCT/JP03/04964

§ 371 (c)(1),
(2), (4) Date: Oct. 25, 2004

(87) PCT Pub. No.: WO03/092505

PCT Pub. Date: Nov. 13, 2003

(65) Prior Publication Data

US 2005/0131297 A1 Jun. 16, 2005

(30) Foreign Application Priority Data

Apr. 30, 2002 (JP) ............................. 2002-128522

(51) Int. Cl.
*A61B 8/00* (2006.01)

(52) U.S. Cl. ......................... 600/443; 600/459; 73/618; 73/626

(58) Field of Classification Search ................. 600/443, 600/459; 73/1.82, 618, 626
See application file for complete search history.

(56) References Cited

U.S. PATENT DOCUMENTS

| | | | | |
|---|---|---|---|---|
| 5,617,862 | A * | 4/1997 | Cole et al. | 600/459 |
| 5,655,536 | A * | 8/1997 | Takamizawa | 600/447 |
| 5,673,699 | A * | 10/1997 | Trahey et al. | 600/447 |
| 5,740,806 | A * | 4/1998 | Miller | 600/459 |
| 6,030,344 | A * | 2/2000 | Guracar et al. | 600/447 |
| 6,146,329 | A * | 11/2000 | Hayakawa | 600/443 |
| 6,203,498 | B1 * | 3/2001 | Bunce et al. | 600/446 |
| 6,436,047 | B1 * | 8/2002 | Ramamurthy et al. | 600/447 |
| 6,491,633 | B1 * | 12/2002 | Krishnan et al. | 600/447 |
| 6,540,677 | B1 * | 4/2003 | Angelsen et al. | 600/437 |

FOREIGN PATENT DOCUMENTS

| | | |
|---|---|---|
| JP | 7-67879 | 3/1995 |
| JP | 2000-152937 | 6/2000 |
| JP | 2001-276064 | 10/2001 |

* cited by examiner

*Primary Examiner*—Ruth S Smith
*Assistant Examiner*—Jonathan G Cwern
(74) *Attorney, Agent, or Firm*—Connolly Bove Lodge & Hutz LLP

(57) ABSTRACT

An ultrasonic diagnostic equipment capable of reducing cost by reducing the number of transmission drive circuits for generating transmission pulse is disclosed. High voltage switches for determining an aperture by selecting eight pieces from among transducer elements to which transmission pulses are applied, and low voltage switches for selecting 16 pieces from among the transducer elements to receive ultrasonic echo are provided individually. Regarding the high voltage switches for transmission, four inputs are integrated into one, and a distribution circuit of 1:4 is constructed. Regarding the low voltage switches for reception, two outputs are integrated into one, and a multiplexer of 2:1 is constructed. Linear scanning is performed by only eight pulsers (transmission drive circuits). The high voltage switches for transmitting ultrasonic waves and the low voltage switches for receiving ultrasonic waves are separated from each other.

11 Claims, 13 Drawing Sheets

ULTRASONIC DIAGNOSTIC EQUIPMENT

TECHNICAL FIELD

The present invention relates to an ultrasonic diagnostic equipment, and more particularly to an ultrasonic diagnostic equipment for performing linear scanning by using arrayed transducer elements.

BACKGROUND ART

An ultrasonic diagnostic equipment is an equipment for observing an internal state of an examination object by transmitting an ultrasonic wave from an ultrasonic probe (probe) arraying ultrasonic transducer elements into the examination object, receiving at the ultrasonic probe the ultrasonic wave returned after being reflected inside the examination object, and signal-processing and imaging the received ultrasonic wave. As an ultrasonic beam control method in the ultrasonic diagnostic equipment, there are sector scanning method and linear scanning method. The sector scanning method is a scanning method, wherein a measurement cross sectional layer is expressed as polar coordinates, a wave transmitting position of an ultrasonic wave is set to an origin, a traveling direction of the ultrasonic wave is designated as a diameter direction, and a wave transmitting direction is designated as an angle direction. The linear scanning method is a scanning method, wherein a measurement cross sectional layer is expressed as Cartesian coordinates, a traveling direction of an ultrasonic wave is designated as one axis, and a wave transmitting position of the ultrasonic wave is moved on the other orthogonal axis.

In an ultrasonic diagnostic equipment for performing the linear scanning by using arrayed transducer elements of an ultrasonic probe, focusing technique, in which convergence of ultrasonic beam is performed by using the plurality of arrayed transducer elements concurrently is utilized. There is transmission focusing technique, wherein control is made so that ultrasonic beam is converged at a certain test part in the body by shifting generation start timing of pulse given to respective transducer elements of an ultrasonic probe. Further, there is an ultrasonic diagnostic equipment for performing synthetic aperture scanning.

Descriptions will be hereinafter given of the focusing technique briefly. A transmission timing signal is output from a transmission timing control circuit to a driver at a timing that ultrasonic beam concurrently reaches the part where the ultrasonic beam is desired to be converged. The driver generates ultrasonic transmission pulse according to the transmission timing signal, and transmits the ultrasonic transmission pulse to a transducer element. Each driver and each transducer element are connected one for one. A signal converted to an ultrasonic wave at the transducer element is reflected inside the examination object, converted to an electrical signal at the transducer element, and delay-added at a reception beam forming device.

In the synthetic aperture scanning, drive pulse is generated in a transmission circuit, and a selected transducer element is driven. The transducer element generates ultrasonic pulse, and ultrasonic pulse reflected inside the examination object is received at the transducer element as an echo ultrasonic wave. The receiver signal is amplified, converted to digital data, and written in a memory. After writing in the memory is finished, a different transducer element is selected, and a receiver signal is written in the memory as above. The respective receiver signals stored in the memory are added with a given time difference. The added receiver signals are signal-processed at a signal processor, and shown on a display part. When the examination object remains stationary during reception, a signal from a specific inner part of the examination object can be emphasized, and sharp reception directivity can be obtained. Some examples of conventional ultrasonic diagnostic equipments will be hereinafter cited.

"Ultrasonic diagnostic equipment" disclosed in Japanese Unexamined Patent Application Publication No. H07-67879 is an ultrasonic diagnostic equipment for performing the synthetic aperture, wherein image deterioration caused by motion of an examination object is prevented. Arrayed transducer elements are driven by a transmission circuit, and ultrasonic waves are transmitted into an examination object. Among echoes respectfully received by the transducer elements, one or more signals from one or more given transducer elements is/are selected by switches. The signal is appropriately amplified at an amplifier, converted to a digital signal at an A/D converter, and then delay-added at a beam synthetic part, and stored in a memory. As above, an ultrasonic wave is transmitted again, and a signal of other transducer element is selected by a switch. Similar signal processing is performed at the amplifier, the A/D converter, and the beam synthetic part, and then the signal is added to the delay-added signal which has been stored in the memory. These added signals are provided with signal processing at a signal processing part, and then shown on a display part.

"Ultrasonic diagnostic equipment" disclosed in Japanese Unexamined Patent Application Publication No. 2000-152937 is an ultrasonic diagnostic equipment, wherein the number of transmission drivers is reduced without losing a shape of reception beam. By inserting a switch (diode) between the transmission driver and a transducer element, a plurality of transducer elements can be driven by one driver. In reception, signals of the respective transducer elements can be processed independently.

A concrete example of the conventional ultrasonic diagnostic equipment which performs the linear scanning will be hereinafter described with reference to FIG. 13. FIG. 13 is a block diagram of a front end part of the ultrasonic diagnostic equipment. In FIG. 13, a probe 1 is an ultrasonic probe comprising an array of transducer elements 2-1 to 2-32. The transducer elements 2-1 to 2-32 are actuators/sensors for transmitting and receiving ultrasonic waves. High voltage switches 3-1 to 3-32 are switches for selecting transducer elements corresponding to an aperture to be used, and applying high voltage transmission pulse. Pulsers 4-1 to 4-16 are transmission drive circuits generating transmission pulse. A trigger generator 5 is a means for generating transmission trigger signals. Limiters 6-1 to 6-16 are means for clipping the high voltage transmission pulse to protect subsequent stage circuits. A cross point switch (CPS) 7 is a means for sorting and adding limiter outputs. A/D converters 8-1 to 8-8 are means for converting analog receiver signals to digital signals. A beam forming device 9 is a means for delay-adding the digital converted data. A controller 10 is a means for performing timing control of a transmission circuit and a reception circuit.

Operation of the conventional ultrasonic diagnostic equipment constructed as above will be hereinafter described. The trigger generator 5 generates a transmission trigger signal, a timing signal for outputting ultrasonic pulse. According to the transmission trigger signal, the pulsers 4-1 to 4-16 generate transmission pulse. In order to protect circuits such as the subsequent stage cross point switch from high voltage transmission pulse generated at the pulsers 4-1 to 4-16, the limiters 6-1 to 6-16 clip the high voltage transmission pulse to enter the cross point switch 7. By selectively turning ON/OFF the high voltage switches 3-1 to 3-32, the high voltage transmission pulse is applied to only transducer elements to be driven. By this selective operation, a position and a width of an aperture of the probe 1 are determined. Selected 16 transducer elements of the probe 1 transmit ultrasonic waves to the examination object.

Reflected ultrasonic waves from the examination object are received at the transducer elements 2-1 to 2-32. The receiver signals pass selected 16 high voltage switches, enter the cross point switch 7 via the limiters 6-1 to 6-16. At the cross point switch 7, the receiver signals are sorted and added, and then changed into eight synthetic receiver signals. The synthetic receiver signals are converted to digital signals at the A/D converters 8-1 to 8-8. The digital converted receiver signals are delay-added and directivity is adjusted at the beam forming device 9. The resultant output signal is converted to an image signal at an unshown circuit, and displayed. The controller 10 performs timing control of the transmission circuit and the reception circuit of the ultrasonic waves.

In the foregoing conventional ultrasonic diagnostic devices, however, many circuits are required, and therefore, there is a problem that manufacturing the conventional ultrasonic diagnostic device is costly. In particular, there is a problem that manufacturing the transmission drive circuit (pulser) for generating transmission pulse is significantly costly.

DISCLOSURE OF THE INVENTION

It is an object of the invention to provide an ultrasonic diagnostic equipment, which can solve the foregoing conventional problems and perform linear scanning with few transmission drive circuits.

In order to solve the foregoing tasks, in the invention, the ultrasonic diagnostic equipment is an ultrasonic diagnostic equipment comprising; a plurality of arrayed ultrasonic transducer elements, a plurality of transmission drive circuits for driving the ultrasonic transducer elements, a plurality of high voltage switches for connecting the ultrasonic transducer elements and the transmission drive circuits, a plurality of limiters for clipping transmission pulse having a given voltage or more, which is generated at the transmission drive circuits, a cross point switch which has input terminals whose number is larger than the number of the transmission drive circuits, and performs sorting and adding signals received at the ultrasonic transducer elements, low voltage switches for connecting output signals of the limiters to the input terminals of the cross point switch, A/D converters for converting output signals of the cross point switch to digital signals, and a beam forming device for delay-adding the output signals of the A/D converters, wherein:

an ultrasonic pulse transmission circuit has fewer channels than a reception circuit. Since the ultrasonic diagnostic equipment is constructed as above, connection patterns of the high voltage switch for transmission and connection patterns of the low voltage switches for reception can be changed independently, and linear scanning with sufficient precision can be performed even with few transmission drive circuits.

Further, the ultrasonic diagnostic equipment comprises a means for changing connection patterns of the high voltage switches, and a means for turning ON/OFF the high voltage switches by a connection pattern with which an aperture wider than a minimum aperture determined by the number of the transmission drive circuits is obtained. Since the ultrasonic diagnostic equipment is constructed as above, an aperture wider than a minimum aperture determined by the number of the transmission drive circuits can be obtained by changing connection methods of the high voltage switches for transmission. In particular, when focus is set at the deep part, a beam shape can be improved.

Further, the ultrasonic diagnostic equipment comprises a means for identifying a type of a probe connected, and a means for changing a size of the aperture according to the type of the probe. Since the ultrasonic diagnostic equipment is constructed as above, an optimum aperture diameter corresponding to a probe can be obtained by changing connection methods of the high voltage switches for transmission according to probe types, and a beam shape can be improved.

Further, the ultrasonic diagnostic equipment comprises a means for inputting a displayed depth, and a means for changing a size of the aperture according to the input displayed depth. Since the ultrasonic diagnostic equipment is constructed as above, an optimal aperture diameter corresponding to a probe can be obtained by changing connection methods of the high voltage switches for transmission according to displayed depths, and a beam shape can be improved.

Further, the ultrasonic diagnostic equipment comprises a means for inputting a display mode, and a means for changing a size of the aperture according to the input display mode. Since the ultrasonic diagnostic equipment is constructed as above, an optimal aperture diameter corresponding to a probe can be obtained by changing connection methods of the high voltage switches for transmission according to display modes, and a beam shape can be improved.

Further, the ultrasonic diagnostic equipment comprises a means for inputting a transmission focus depth, and a means for changing a size of the aperture according to the input transmission focus depth. Since the ultrasonic diagnostic equipment is constructed as above, an optimal aperture diameter corresponding to a probe can be obtained by changing connection methods of the high voltage switches for transmission according to transmission focus depths, and a beam shape can be improved.

Further, the ultrasonic diagnostic equipment comprises a means for inputting a center frequency of transmission pulse, and a means for changing a size of the aperture according to the input center frequency. Since the ultrasonic diagnostic equipment is constructed as above, an optimal aperture diameter corresponding to a probe can be obtained by changing connection methods of the high voltage switches for transmission according to center frequencies of transmission pulse, and a beam shape can be improved.

Further, the ultrasonic diagnostic equipment comprises a means for selecting whether a higher resolution is prioritized or whether a wider dynamic range is prioritized, and a means for selecting transducer elements to be used according to characteristics to be prioritized. Since the ultrasonic diagnostic equipment is constructed as above, one of resolution improvement and side lobes reduction can be selected by selecting whether transducer elements not used are gathered in the vicinity of center or gathered at end parts when an aperture diameter is widened larger than a minimum aperture determined by the number of the transmission drive circuits. Therefore, an image capable of being easily diagnosed can be displayed.

Further, in the ultrasonic diagnostic equipment, a memory for storing data for one sound ray, and an adder for adding an output of the memory and an output of the beam forming device are provided on the output side of the beam forming device. Since the ultrasonic diagnostic equipment is constructed as above, an optimal beam shape can be realized by performing aperture synthesis by driving transducer elements separated in two groups.

Further, in the ultrasonic diagnostic equipment, high voltage switches for connecting two adjacent transducer elements are provided. Since the ultrasonic diagnostic equipment is constructed as above, transducer elements, whose number is at maximum twice as many as the number of transmission drive circuits, can be concurrently driven. In particular, when focus is set at a deep part, a beam shape can be improved, and a high image quality can be obtained.

Further, in the ultrasonic diagnostic equipment, diodes are inserted between the high voltage switches and the transducer elements. Since the ultrasonic diagnostic equipment is constructed as above, reception channels can be separated, and an optimum beam shape can be realized.

BEST MODE FOR CARRYING OUT THE INVENTION

Detailed descriptions will be hereinafter given of ultrasonic diagnostic equipments of embodiments of the invention with reference to FIGS. 1 to 12.

First Embodiment

A first embodiment of the invention is an ultrasonic diagnostic equipment, wherein switches for selecting transducer elements to transmit ultrasonic waves are separated from switches for selecting transducer elements to receive the ultrasonic waves.

Figure 1:
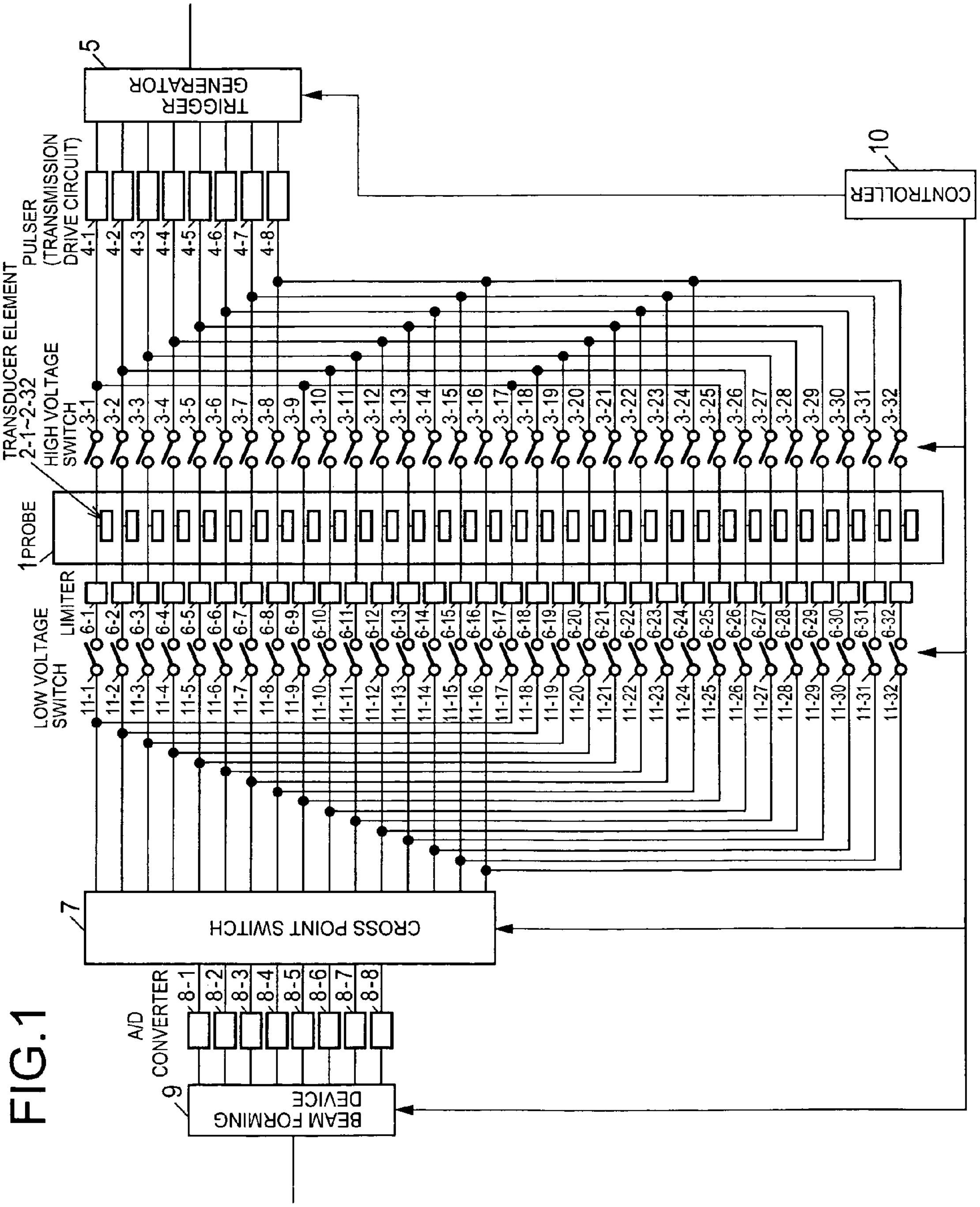
FIG. 1 is a block diagram of a front end part of an ultrasonic diagnostic equipment in a first embodiment of the invention.

FIG. 1 is a block diagram of a transmission/reception circuit of the ultrasonic diagnostic equipment in the first embodiment of the invention. In FIG. 1, a probe 1 is an ultrasonic probe comprising an array of transducer elements 2-1 to 2-32. The transducer elements 2-1 to 2-32 are actuators/sensors for transmitting and receiving ultrasonic waves. High voltage switches (HV-SW) 3-1 to 3-32 are switches for selecting transducer elements corresponding to an aperture to be used and applying high voltage transmission pulse. Pulsers 4-1 to 4-8 are transmission drive circuits for generating the high voltage transmission pulse. A trigger generator 5 is a means for generating a transmission trigger signal, a timing signal to output ultrasonic pulse. Limiters 6-1 to 6-32 are means for clipping (limit a voltage value) the high voltage transmission pulse to enter a cross point switch 7 in order to protect circuits such as the subsequent stage cross point switch 7 from the high voltage transmission pulse generated in the pulsers 4-1 to 4-8. The cross point switch 7 is a means for sorting and adding output signals of the limiters 6-1 to 6-32 to obtain synthetic receiver signals. A/D converters 8-1 to 8-8 are means for converting the analog synthetic receiver signals to digital signals. A beam forming device 9 is a means for delay-adding the digital converted synthetic receiver signals and adjusting directivity. A controller 10 is a means for performing timing control of a transmission circuit and a reception circuit of ultrasonic waves. Low voltage switches (LV-SW) 11-1 to 11-16 are switches for selecting receiver signals to be used from among the output signals of the limiters 6-1 to 6-32.

Operation of the ultrasonic diagnostic equipment in the first embodiment of the invention constructed as above will be hereinafter described. It is different from conventional equipments that the high voltage switches 3-1 to 3-32 for selecting transducer elements to transmit ultrasonic pulse are separated from the low voltage switches 11-1 to 11-16 for selecting transducer elements which has received ultrasonic echo. In the circuit for transmitting ultrasonic pulse, inputs into given four of the high voltage switches 3-1 to 3-32 are conducted by a given one of the pulsers 4-1 to 4-8, and a distribution circuit of 1:4 is constructed. Therefore, when the ultrasonic pulse is transmitted, 32 pieces of the transducer elements 2-1 to 2-32 can be driven by the eight pulsers, and therefore, linear scanning is enabled. In the circuit for receiving ultrasonic echo, every two outputs of the low voltage switches 11-1 to 11-16 are integrated into one respectively, and a multiplexer of 2:1 is constructed.

It is impossible to adopt dynamic focus as in the case of reception, as a method for adjusting focus in transmitting ultrasonic pulse. Therefore, there are few cases that beam control to focus ultrasonic waves on a point at a target depth by using many channels of transducer elements. Therefore, the number of ultrasonic pulse transmission circuits may be fewer than that of the reception circuit.

The trigger generator 5 generates a transmission trigger signal, a timing signal to output ultrasonic pulse. According to the transmission trigger signal, the pulsers 4-1 to 4-8 generate transmission pulse. By selectively turning ON eight of the high voltage switches 3-1 to 3-32, high voltage transmission pulse is applied to only transducer elements to be driven among the transducer elements 2-1 to 2-32 arrayed in the probe 1. By this selective operation, a position and a width of an aperture of the probe 1 are determined. The selected eight transducer elements of the probe 1 transmit ultrasonic waves to an examination object. In order to protect circuits such as the subsequent stage cross point switch from the high voltage transmission pulse applied to the transducer elements, the limiters 6-1 to 6-32 clips the high voltage transmission pulse to enter the cross point switch 7.

Reflected ultrasonic waves from the examination object are received at the transducer elements 2-1 to 2-32. The receiver signals pass 16 pieces selected from among the low voltage switches 11-1 to 11-32, and enter the cross point switch 7. At the cross point switch 7, the receiver signals are sorted and added, and then changed into eight synthetic receiver signals. At the A/D converters 8-1 to 8-8, the synthetic receiver signals are converted to digital signals. At the beam forming device 9, the digital converted receiver signals are delay-added, and directivity is adjusted. The resultant output signal is converted to an image signal in an unshown circuit, and displayed. The controller 10 performs timing control of the transmission circuit and the reception circuit of the ultrasonic waves.

As mentioned above, in the first embodiment of the invention, the ultrasonic diagnostic equipment has a construction, wherein the switches 3-1 to 3-32 for selecting transducer elements to transmit ultrasonic waves are separated from the switches 11-1 to 11-32 for selecting the transducer elements 2-1 to 2-32 to receive the ultrasonic waves. Therefore, the number of the transmission drive circuits (pulsers) can be reduced, and manufacturing cost can be reduced while performance is maintained.

Second Embodiment

An ultrasonic diagnostic equipment of a second embodiment of the invention will be hereinafter described by using FIGS. 1 and 2. The ultrasonic diagnostic equipment of the second embodiment of the invention is an ultrasonic diagnostic equipment, wherein a connection pattern of high voltage switches for selecting transducer elements to transmit ultrasonic waves is changed at the controller 10 into a connection pattern wherein an aperture wider than a minimum aperture determined by the number of transmission drive circuits can be obtained, and the high voltage switches are turned ON/OFF at the controller 10.

Figure 2:
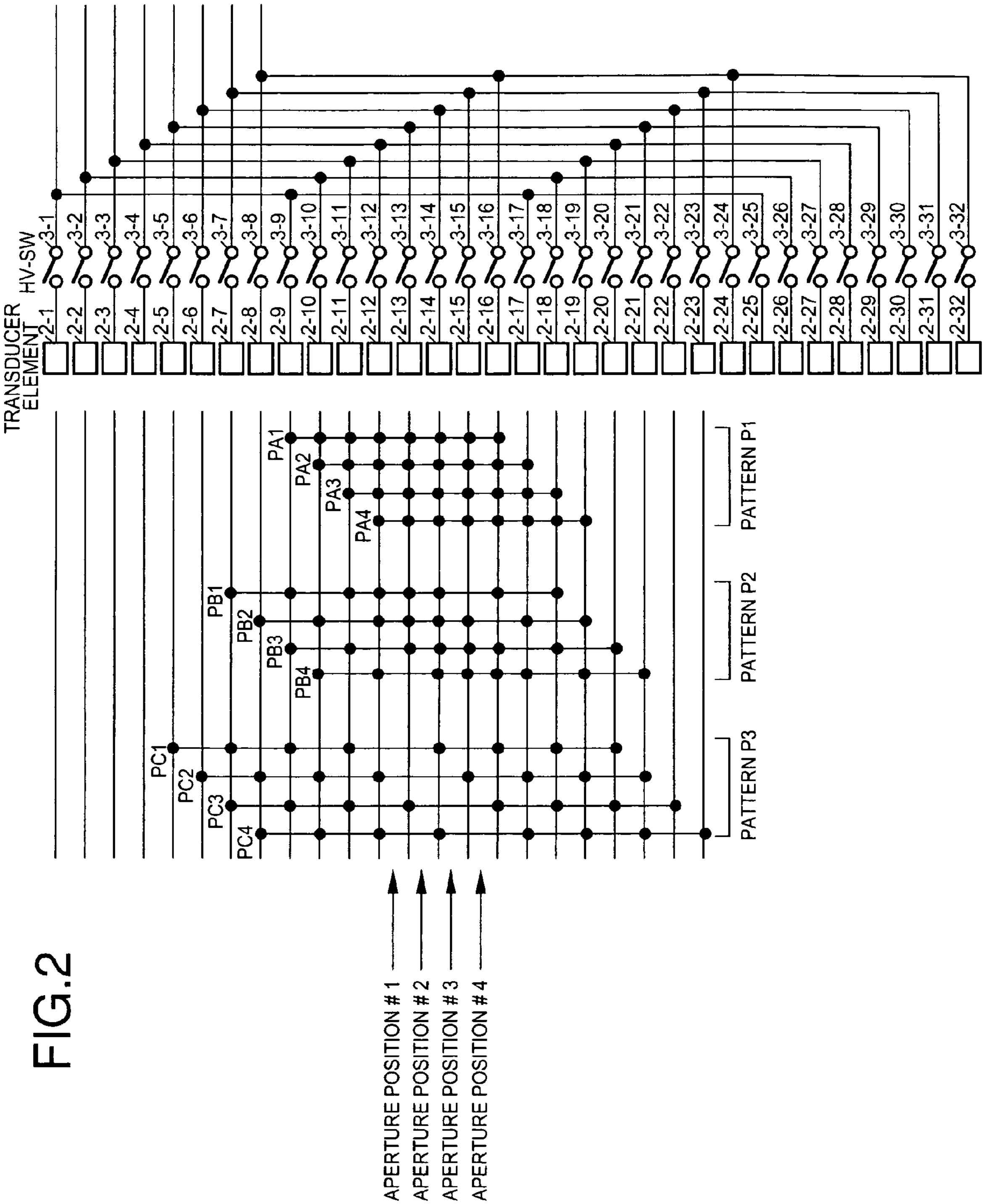
FIG. 2 is an explanation drawing showing a connection of high voltage switches of an ultrasonic diagnostic equipment in a second embodiment of the invention.

FIG. 2 is an explanation drawing of a connection method of the high voltage switches of a transmission circuit of the ultrasonic diagnostic equipment in the second embodiment of the invention. The transducer elements 2-1 to 2-32 are actuators/sensors for transmitting or receiving ultrasonic waves. The high voltage switches (HV-SW) 3-1 to 3-32 are switches for selecting transducer elements corresponding to an aperture to be used and applying high voltage transmission pulse. A general construction of the ultrasonic diagnostic equipment in the second embodiment is similar to of the ultrasonic diagnostic equipment in the first embodiment shown in FIG. 1.

Operation of the ultrasonic diagnostic equipment in the second embodiment of the invention constructed above will be hereinafter described. By changing ON/OFF patterns of the high voltage switches, an aperture wider than a minimum aperture determined by the number of the transmission drive circuits (8) (8 in units of array pitch of the transducer elements) is realized. Pattern P1 is a regular switch connection pattern. ● mark indicates a position of a switch to be turned ON. An aperture is a minimum aperture (8), which is determined by the number of the transmission drive circuits (8). In PA1 of Pattern P1, a center of the aperture becomes Aperture position #1. In PA2 of Pattern P1, a center of the aperture becomes Aperture position #2. In PA3 of Pattern P1, a center of the aperture becomes Aperture position #3. In PA4 of Pattern P1, a center of the aperture becomes Aperture position #4.

In Pattern P2, a width of an aperture becomes 12. In PB1 of Pattern 2, a center of the aperture becomes Aperture position #1. In PB2 of Pattern 2, a center of the aperture becomes Aperture position #2. In PB3 of Pattern 2, a center of the aperture becomes Aperture position #3. In PB4 of Pattern 2, a center of the aperture becomes Aperture position #4. In Pattern P3, a width of an aperture becomes 16. In PC1 of Pattern 3, a center of the aperture becomes Aperture position #1. In PC2 of Pattern 3, a center of the aperture becomes Aperture position #2. In PC3 of Pattern 3, a center of the aperture becomes Aperture position #3. In PC4 of Pattern 3, a center of the aperture becomes Aperture position #4.

As above, by changing positions of ON connection of the high voltage switches for selecting transducer elements to transmit ultrasonic waves, an aperture wider than the minimum aperture (8) determined by the number of the transmission drive circuits (8) can be realized. When a wider aperture is required since, for example, a channel pitch of the transducer elements of the probe 1 is narrow, the aperture can be easily widened.

As mentioned above, in the second embodiment of the invention, the ultrasonic diagnostic equipment has a construction, wherein the connection pattern of the high voltage switches is changed, and the high voltage switches are turned ON/OFF by the connection pattern wherein an aperture becomes wider than the minimum aperture determined by the number of the transmission drive circuits. Therefore, the number of the transmission drive circuits (pulsers) can be reduced, and an inexpensive ultrasonic diagnostic equipment can be realized while performance is maintained.

Third Embodiment

A third embodiment of the invention is an ultrasonic diagnostic equipment, wherein an ID generator is provided in a probe, and an ID encoder is provided in an equipment body.

Figure 3:
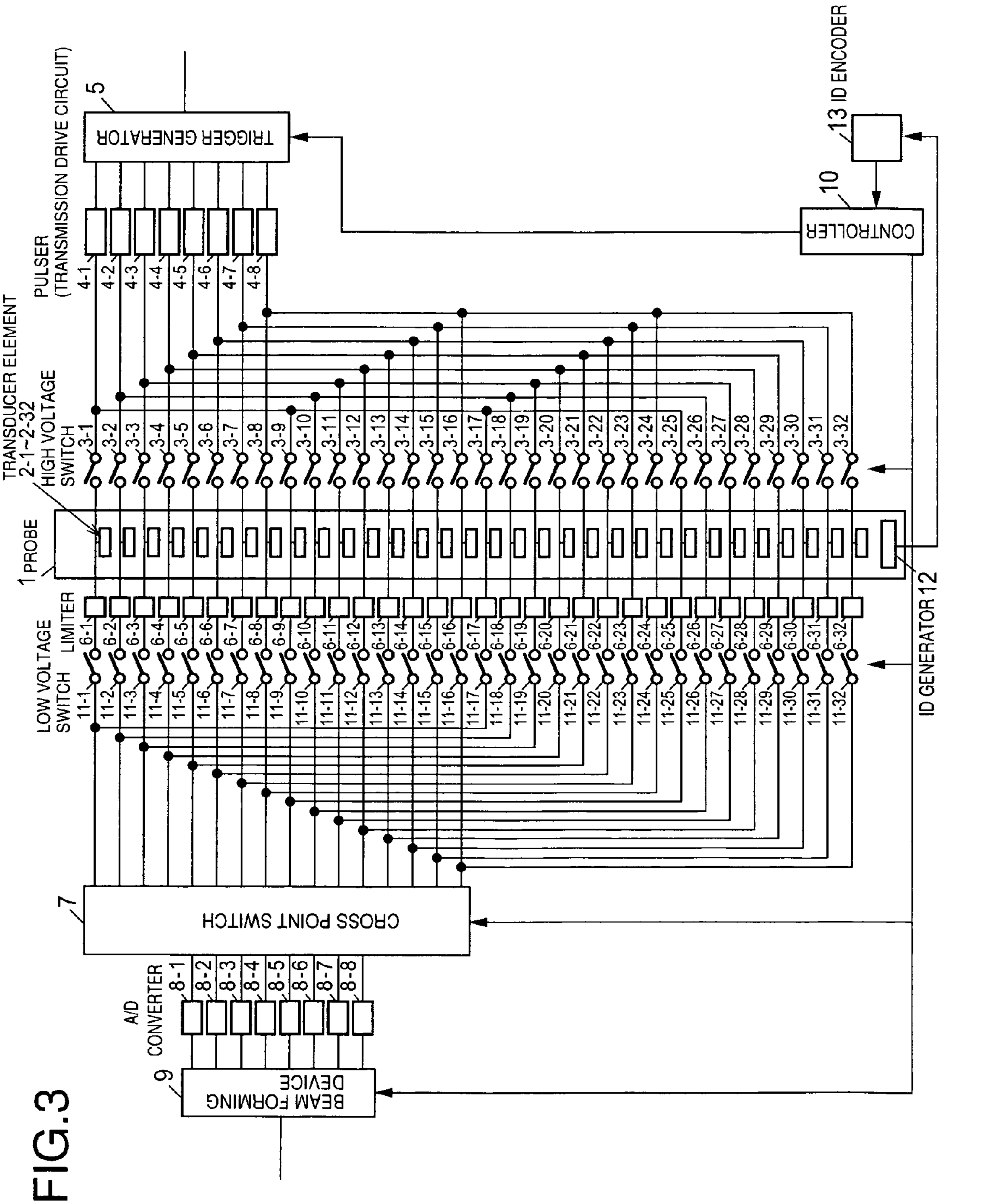
FIG. 3 is a block diagram of a front end part of an ultrasonic diagnostic equipment in a third embodiment of the invention.

FIG. 3 is a block diagram of a transmission/reception circuit of the ultrasonic diagnostic equipment in the third embodiment of the invention. In FIG. 3, an ID generator 12 is a means for generating an identification code representing a probe type. An ID encoder 13 is a means for converting the identification code to a control signal. A general construction of the ultrasonic diagnostic equipment in the third embodiment is similar to of the ultrasonic diagnostic equipment in the first embodiment shown in FIG. 1, except that the ID generator 12 is provided in the probe 1 and the ID encoder 13 is provided in the equipment body.

Operation of the ultrasonic diagnostic equipment in the third embodiment of the invention constructed as above will be hereinafter described. When the probe 1 is connected to the equipment body, the ID generator 12 generates an identification code representing a probe type, and transmits the generated identification code to the ID encoder 13 provided in the equipment body. The ID encoder 13 converts the identification code to a control signal, and outputs the control signal to the controller 10. As above, the probe type is read by the controller 10 by using the ID generator 12 and the ID encoder 13. The controller 10 controls an aperture diameter of ultrasonic beam by changing patterns of ON connection of the high voltage switches 3-1 to 3-32 according to probe types.

As described above, in the third embodiment of the invention, the ultrasonic diagnostic equipment has a construction, wherein the ID generator is provided in the probe and the ID encoder is provided in the equipment body. Therefore, an optimum aperture diameter can be realized for each probe, a transmission circuit amount can be reduced, and an inexpensive ultrasonic diagnostic equipment can be realized while performance is maintained.

Fourth Embodiment

A fourth embodiment of the invention is an ultrasonic diagnostic equipment, wherein a displayed depth input equipment is added.

Figure 4:
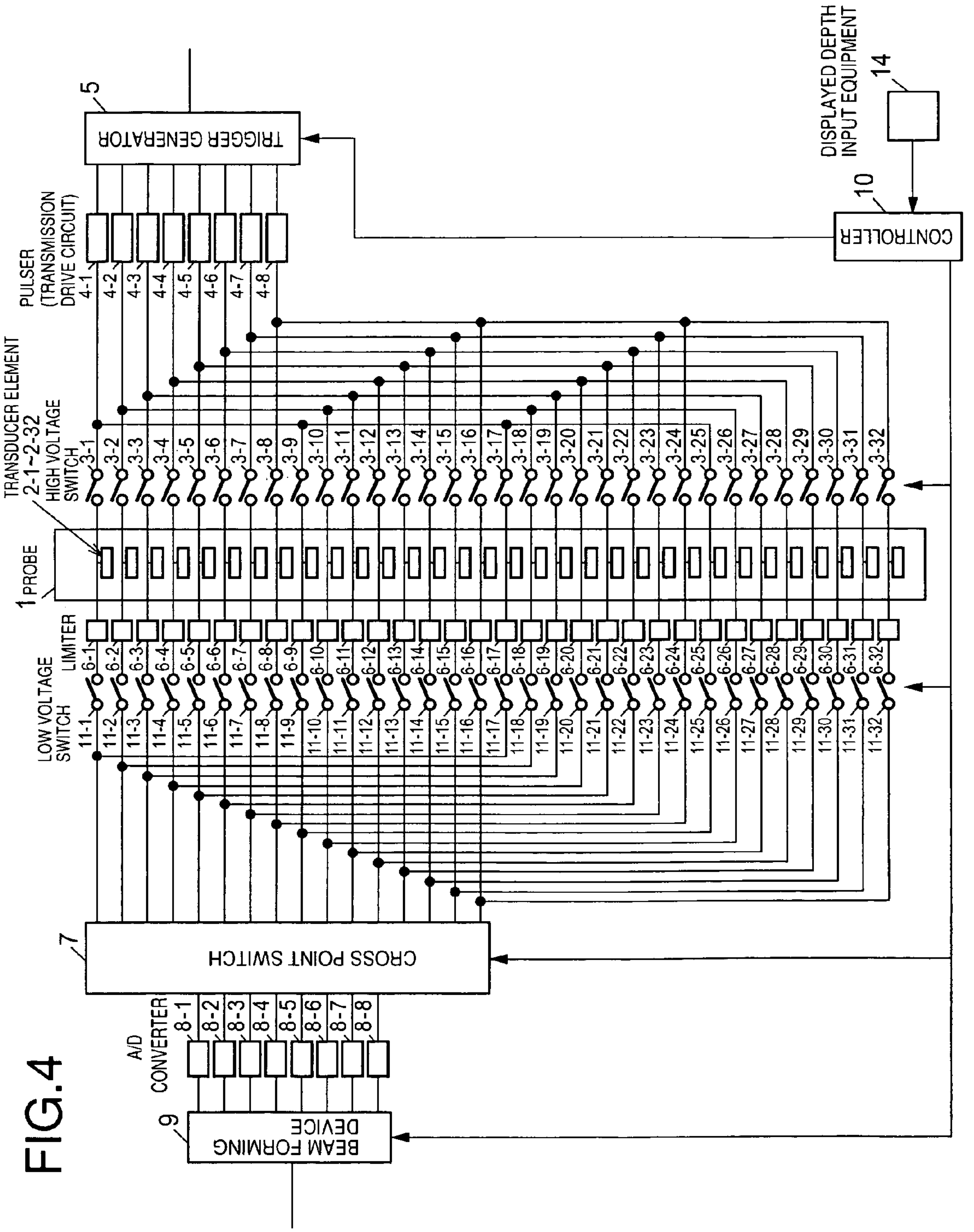
FIG. 4 is a block diagram of a front end part of an ultrasonic diagnostic equipment in a fourth embodiment of the invention.

FIG. 4 is a block diagram of a transmission/reception circuit of the ultrasonic diagnostic equipment in the forth embodiment of the invention. In FIG. 4, a displayed depth input equipment 14 is a means for inputting data which indicates a target displayed depth. A general construction of the ultrasonic diagnostic equipment in the forth embodiment is similar to of the ultrasonic diagnostic equipment in the first embodiment shown in FIG. 1, except that the displayed depth input equipment 14 is added.

Operation of the ultrasonic diagnostic equipment in the forth embodiment of the invention constructed as above will be hereinafter described. The displayed depth input equipment 14 provides the controller 10 with displayed depth information. The controller 10 controls an aperture diameter of ultrasonic beam by changing patterns of ON connection of the high voltage switches 3-1 to 3-32 according to displayed depths. When a deep part is displayed, the pattern of ON connection of the high voltage switches 3-1 to 3-32 is changed so that the aperture diameter of ultrasonic beam can be widened. When a shallow part is displayed, the pattern of ON connection of the high voltage switches 3-1 to 3-32 is changed so that the aperture diameter of ultrasonic beam can be narrowed.

As mentioned above, in the fourth embodiment of the invention, the ultrasonic diagnostic equipment has a construction, wherein the displayed depth input equipment is added. Therefore, an optimum aperture diameter can be realized for each displayed depth, a transmission circuit amount can be reduced, and an inexpensive ultrasonic diagnostic equipment can be realized while performance is maintained.

Fifth Embodiment

A fifth embodiment of the invention is an ultrasonic diagnostic equipment, wherein a display mode input equipment is added.

Figure 5:
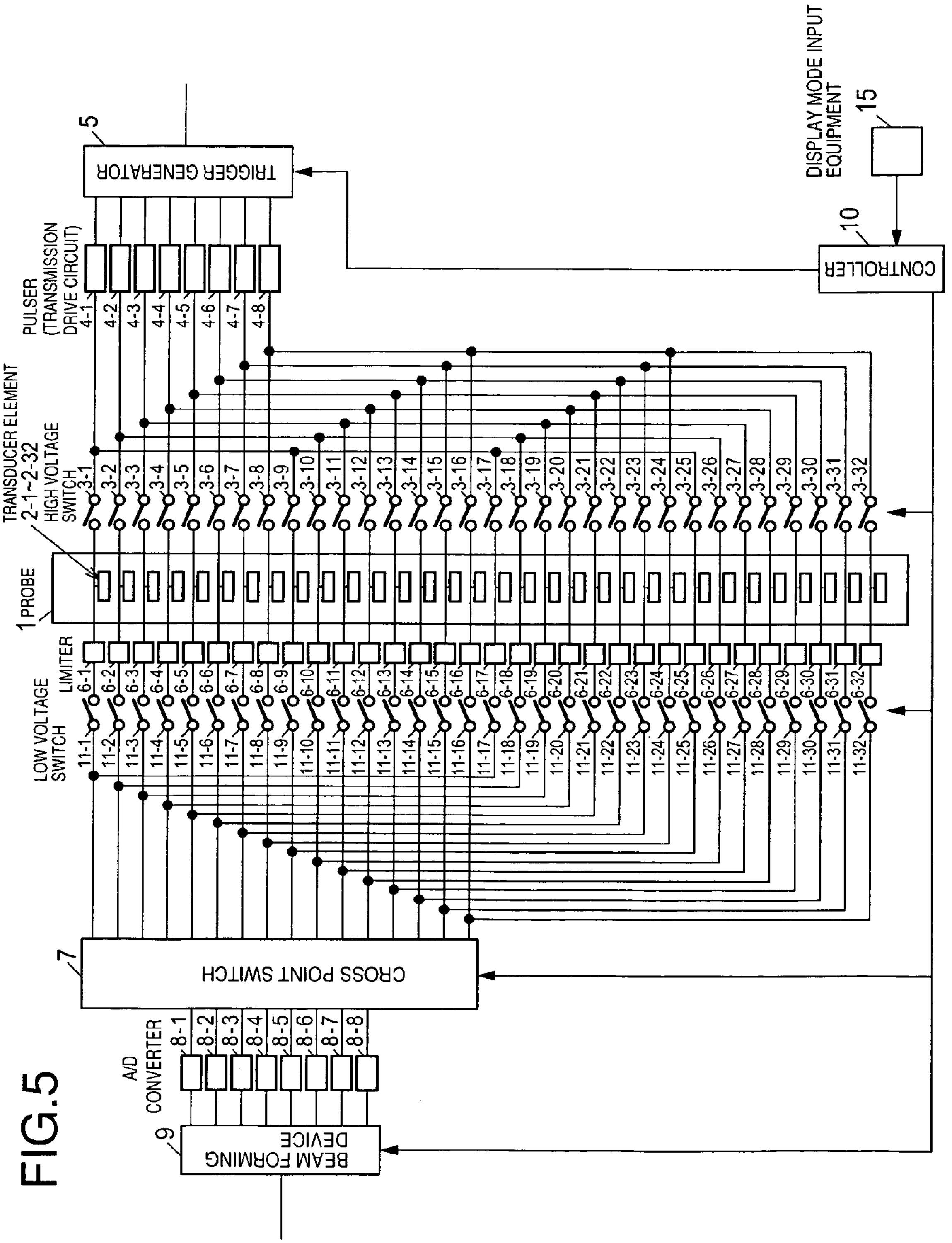
FIG. 5 is a block diagram of a front end part of an ultrasonic diagnostic equipment in a fifth embodiment of the invention.

FIG. 5 is a block diagram of a transmission/reception circuit of the ultrasonic diagnostic equipment in the fifth embodiment of the invention. In FIG. 5, a display mode input equipment 15 is a means for inputting data which indicates a target display mode. A general construction of the ultrasonic diagnostic equipment in the fifth embodiment is similar to of the ultrasonic diagnostic equipment in the first embodiment shown in FIG. 1, except that the display mode input equipment 15 is added.

Operation of the ultrasonic diagnostic equipment in the fifth embodiment of the invention constructed as above will be hereinafter described. In the ultrasonic diagnostic equipment, there are various signal processing/display modes such as B mode, color Doppler mode, and pulse Doppler mode. Optimal aperture diameters vary according to the respective modes. The display mode input equipment 15 provides the controller 10 with display mode information. The controller 10 controls aperture diameters of ultrasonic beam by changing patterns of ON connection of the high voltage switches 3-1 to 3-32 according to display modes.

The B mode is a mode, wherein a pulse transmission position or a pulse transmission direction is moved linearly, and a tomogram of a target in which an envelope curve wave form of an echo receiver signal is intensity-modulated is displayed. When the B mode is used for display, a pattern of ON connection of the high voltage switches 3-1 to 3-32 is changed so that an aperture diameter of ultrasonic beam can be widened.

The color Doppler mode is a mode, wherein a flow rate (average Doppler deflection frequency) in each channel measured on ultrasonic beam is quantized into about eight levels, a flow coming close to the probe is converted to red color luminance information, a flow getting away from the probe is converted to blue color luminance information, and the converted information is shown on a display, while a measurement beam direction is sequentially scanned in color Doppler method which visualizes a flow rate distribution in a two-dimensional fault plane. When the color Doppler mode is used for display, a pattern of ON connection of the high voltage switches 3-1 to 3-32 is changed so that an aperture diameter of ultrasonic beam can be narrowed.

The pulse Doppler mode is a mode for identifying and displaying a reflection part by pulsing transmitted ultrasonic wave by Doppler method. When the pulse Doppler mode is used for display, a pattern of ON connection of the high voltage switches 3-1 to 3-32 is changed so that an aperture diameter of ultrasonic beam can be narrowed.

As mentioned above, in the fifth embodiment of the invention, the ultrasonic diagnostic equipment has a construction, wherein the display mode input equipment is added. Therefore, an optimal aperture diameter can be realized for each display mode, a transmission circuit amount can be reduced, and an inexpensive ultrasonic diagnostic equipment can be realized while performance is maintained.

Sixth Embodiment

A sixth embodiment of the invention is an ultrasonic diagnostic equipment, wherein a transmission focus depth input equipment is added.

Figure 6:
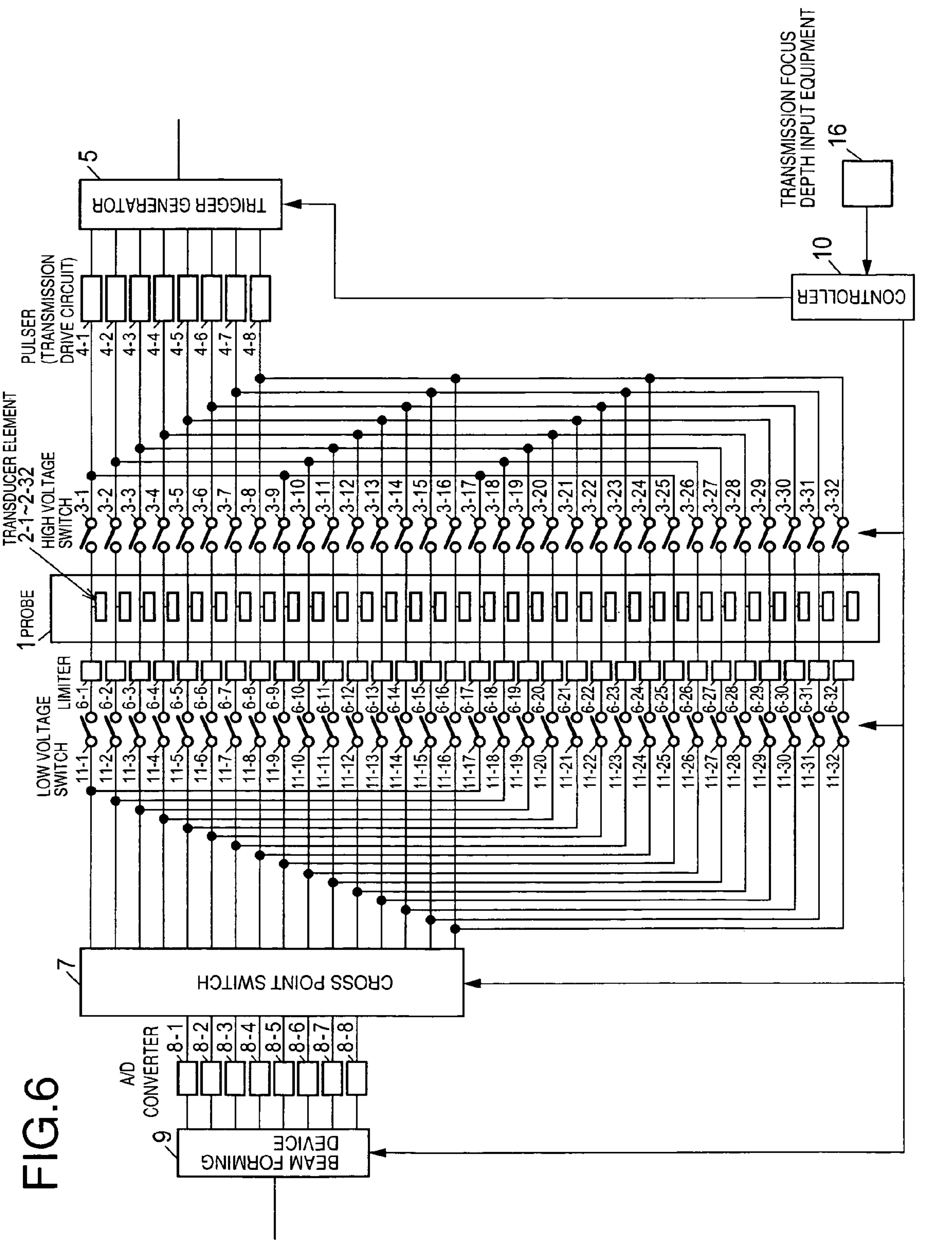
FIG. 6 is a block diagram of a front end part of an ultrasonic diagnostic equipment in a sixth embodiment of the invention.

FIG. 6 is a block diagram of a transmission/reception circuit of the ultrasonic diagnostic equipment in the sixth embodiment of the invention. In FIG. 6, a transmission focus depth input equipment 16 is a means for inputting data which indicates a target transmission focus depth. A general construction of the ultrasonic diagnostic equipment in the sixth embodiment is similar to of the ultrasonic diagnostic equipment in the first embodiment shown in FIG. 1, except that the transmission focus depth input equipment 16 is added.

Operation of the ultrasonic diagnostic equipment in the sixth embodiment of the invention constructed above will be hereinafter described. In the ultrasonic diagnostic equipment, a transmission focus position can be changed even though in the case of the same displayed depth. Optimum aperture diameters vary according to focus depths. The transmission focus depth input equipment 16 inputs data which indicates a target transmission focus depth to the controller 10. The controller 10 controls aperture diameters of ultrasonic beam by changing patterns of ON connection of the high voltage switches 3-1 to 3-32 according to transmission focus depths.

When a deep transmission focus depth is to be obtained, a pattern of ON connection of the high voltage switches 3-1 to 3-32 is changed so that an aperture diameter of ultrasonic beam can be widened. When a shallow transmission focus depth is to be obtained, a pattern of ON connection of the high voltage switches 3-1 to 3-32 is changed so that an aperture diameter of ultrasonic beam can be narrowed.

As mentioned above, in the sixth embodiment of the invention, the ultrasonic diagnostic equipment has a construction, wherein the focus depth input equipment is added. Therefore, an optimal aperture diameter can be realized for each transmission focus depth, a transmission circuit amount can be reduced, and an inexpensive ultrasonic diagnostic equipment can be realized while performance is maintained.

Seventh Embodiment

A seventh embodiment of the invention is an ultrasonic diagnostic equipment, wherein a center frequency input equipment is added.

Figure 7:
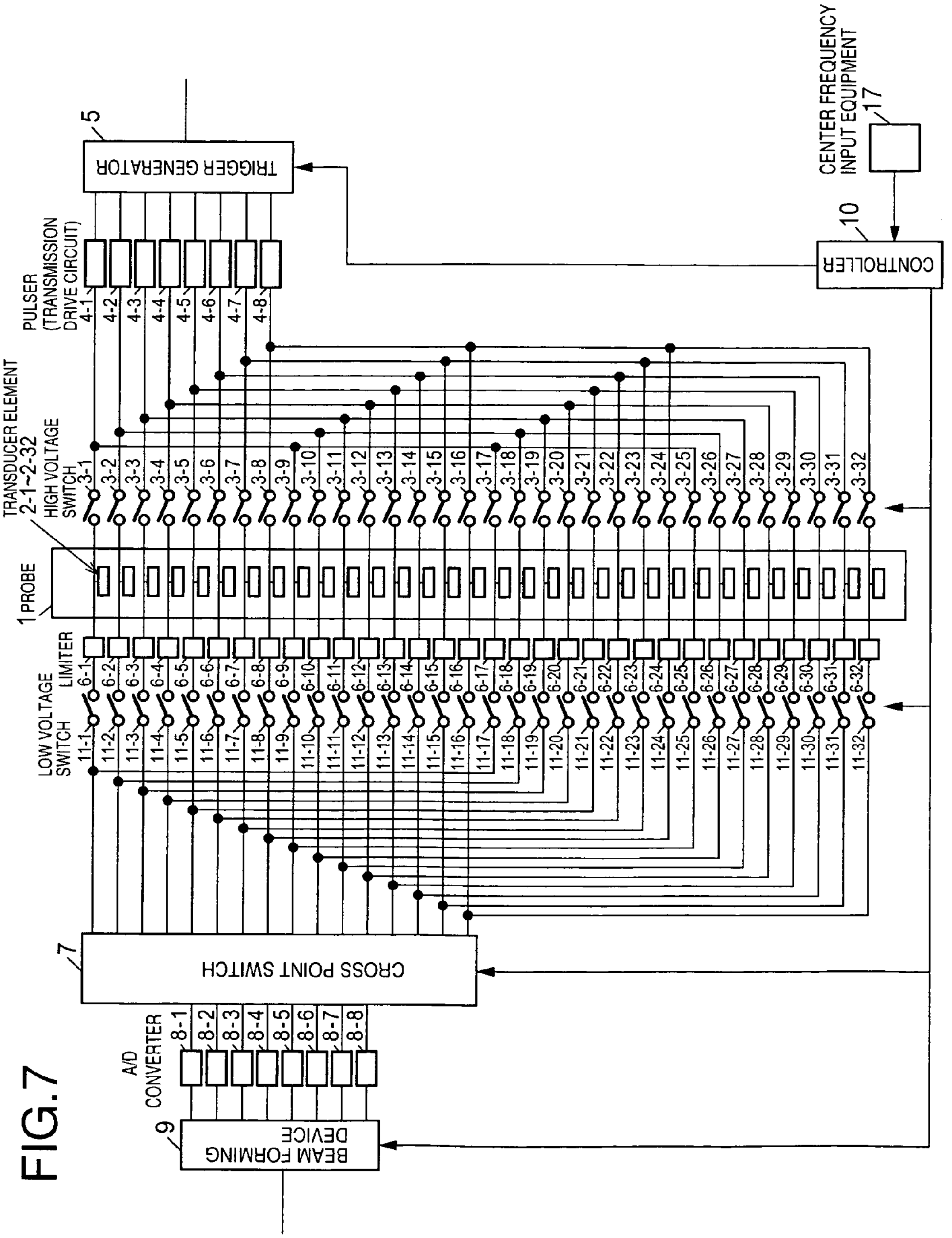
FIG. 7 is a block diagram of a front end part of an ultrasonic diagnostic equipment in a seventh embodiment of the invention.

FIG. 7 is a block diagram of a transmission/reception circuit in the seventh embodiment of the invention. In FIG. 7, a center frequency input equipment 17 is a means for inputting data which indicates a center frequency of transmission pulse. A general construction of the ultrasonic diagnostic equipment in the seventh embodiment is similar to of the ultrasonic diagnostic equipment in the first embodiment shown in FIG. 1, except that the center frequency input equipment 17 is added.

Operation of the ultrasonic diagnostic equipment in the seventh embodiment of the invention constructed above will be hereinafter described. In the ultrasonic diagnostic equipment, center frequency settings of transmission pulse are changed according to examined parts even the same probe is used. Optimum aperture diameters vary according to center frequencies. The center frequency input equipment 17 inputs data which indicates a center frequency of transmission pulse to the controller 10. The controller 10 controls aperture diameters of ultrasonic beam by changing patterns of ON connection of the high voltage switches 3-1 to 3-32 according to center frequencies of transmission pulse.

When a low center frequency of transmission pulse is to be obtained, a pattern of ON connection of the high voltage switches 3-1 to 3-32 is changed so that an aperture diameter of ultrasonic beam can be widened. When a high center frequency of transmission pulse is to be obtained, a pattern of ON connection of the high voltage switches 3-1 to 3-32 is changed so that an aperture diameter of ultrasonic beam can be narrowed.

As mentioned above, in the seventh embodiment of the invention, the ultrasonic-diagnostic equipment has a construction, wherein the center frequency input equipment is added. Therefore, an optimal aperture diameter can be realized for each center frequency, a transmission circuit amount can be reduced, and an inexpensive ultrasonic diagnostic equipment can be realized while performance is maintained.

Eighth Embodiment

An eighth embodiment of the invention is an ultrasonic diagnostic equipment, wherein whether a higher resolution is prioritized or whether a wider dynamic range is prioritized is selected, and transducer elements to be used are selected according to characteristics to be prioritized.

Figure 8:
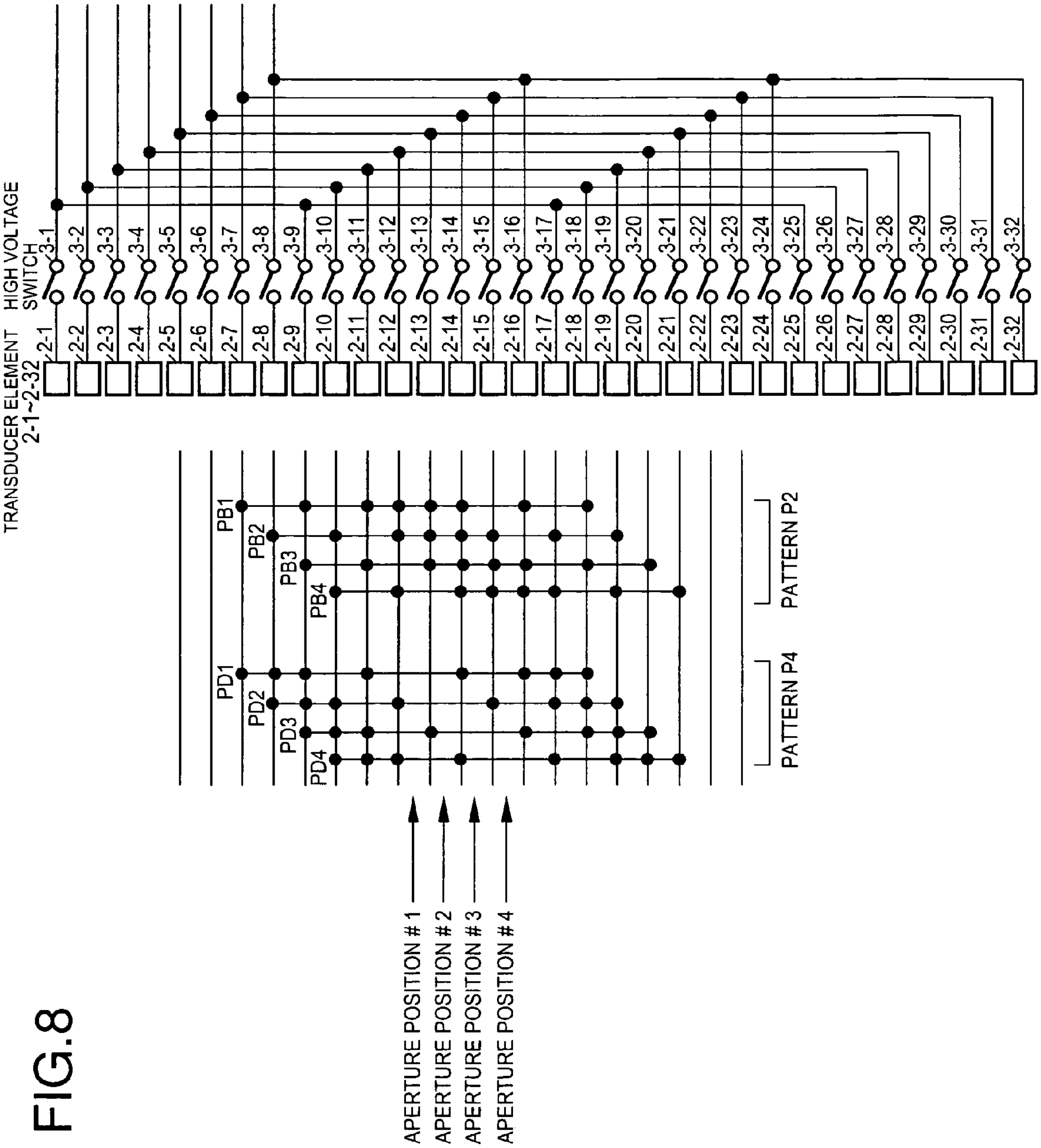
FIG. 8 is an explanation drawing showing a connection of high voltage switches of an ultrasonic diagnostic equipment in an eighth embodiment of the invention.

FIG. 8 is an explanation drawing of a connection method of high voltage switches of a transmission circuit of the ultrasonic diagnostic equipment in the eighth embodiment of the invention. In FIG. 8, the transducer elements 2-1 to 2-32 are actuators/sensors for transmitting or receiving ultrasonic wave. The high voltage switches (HV-SW) 3-1 to 3-32 are switches for selecting transducer elements corresponding to an aperture to be used and applying high voltage transmission pulse. A general construction of the ultrasonic diagnostic equipment in the eighth embodiment is similar to of the ultrasonic diagnostic equipment of the first embodiment shown in FIG. 1.

Operation of the ultrasonic diagnostic equipment in the eighth embodiment of the invention constructed above will be hereinafter described. By changing patterns of ON connection of the high voltage switches 3-1 to 3-32, a beam shape is changed even though in the case of the same aperture diameter. In Pattern P2, transducer elements to be used are placed relatively at the center of the aperture. In Pattern P4, transducer elements to be used are distributed relatively at ends of the aperture. In Pattern P2, a beam shape with few side lobes can be obtained. In Pattern P4, a beam shape with a thin main lobe can be obtained. One of these patterns is selected by changing an unshown switch by an operator.

In Pattern P2, a width of the aperture is 12 pieces when expressing the width by the number of transducer elements to be used, the beam shape with few side lobes can be obtained, and its dynamic range is widened. In PB1 of Pattern P2, a center of the aperture becomes Aperture position #1. In PB2 of Pattern P2, a center of the aperture becomes Aperture position #2. In PB3 of Pattern P2, a center of the aperture becomes Aperture position #3. In PB4 of Pattern P2, a center of the aperture becomes Aperture position #4.

In Pattern P4, a width of an aperture becomes 12 as well. However, the beam shape with a thin main lobe is obtained, and a resolution becomes improved. In PD1 of Pattern 4, a center of the aperture becomes Aperture position #1. In PD2 of Pattern 4, a center of the aperture becomes Aperture position #2. In PD3 of Pattern 4, a center of the aperture becomes Aperture position #3. In PD4 of Pattern 4, a center of the aperture becomes Aperture position #4.

As mentioned above, in the eighth embodiment of the invention, the ultrasonic diagnostic equipment has a construction, wherein whether a higher resolution is prioritized or whether a wider dynamic range is prioritized is selected, and transducer elements to be used are selected according to characteristics to be prioritized. Therefore, the number of the transmission drive circuits (pulsers) can be reduced, and an inexpensive ultrasonic diagnostic equipment can be realized while performance is maintained.

Ninth Embodiment

A ninth embodiment of the invention is an ultrasonic diagnostic equipment, wherein a memory 18 and an adder 19 are added on the output side of a beam forming device.

Figure 9:
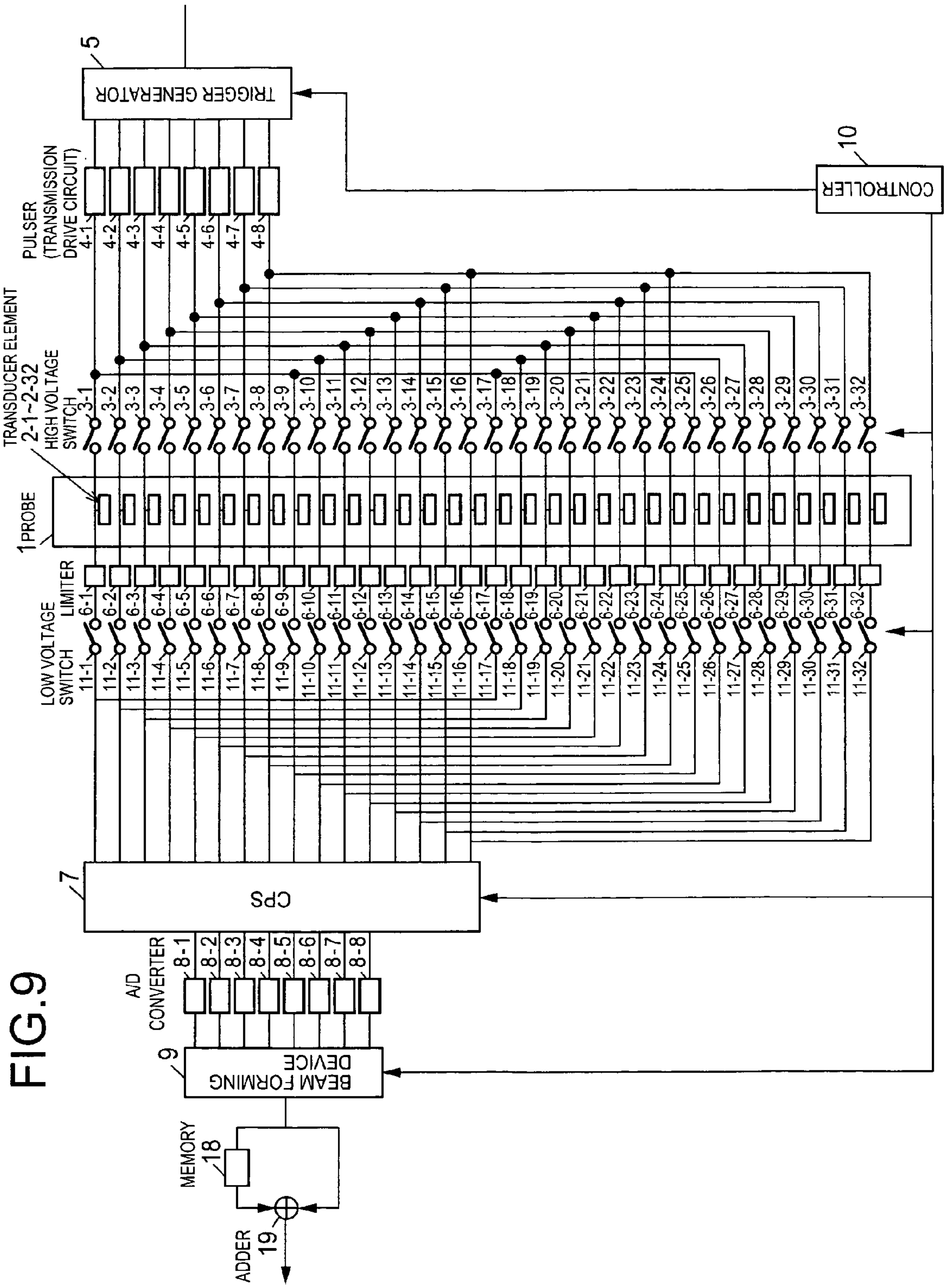
FIG. 9 is a block diagram of a front end part of an ultrasonic diagnostic equipment in a ninth embodiment of the invention.
Figure 10:
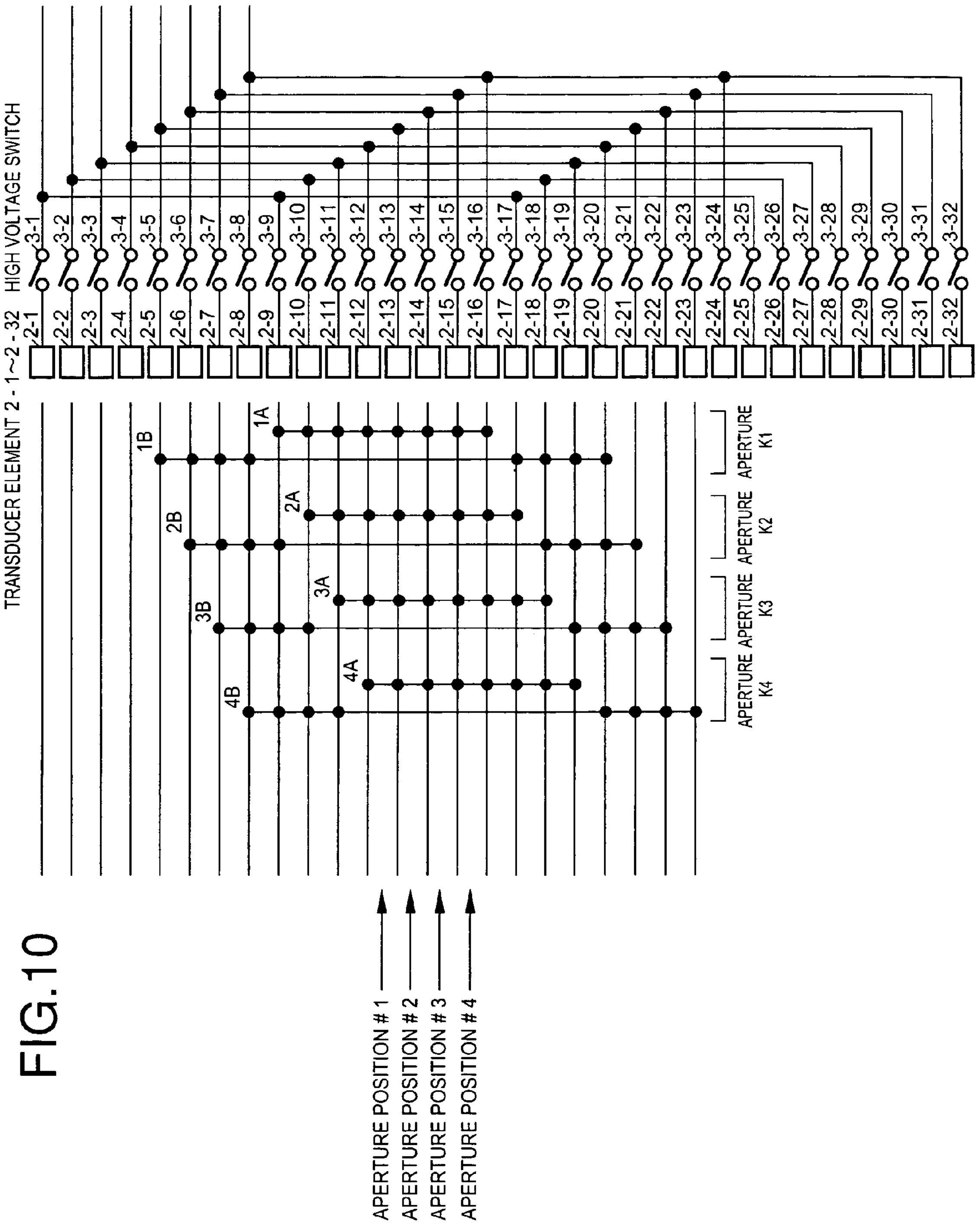
FIG. 10 is an explanation drawing showing a connection of high voltage switches of the ultrasonic diagnostic equipment in the ninth embodiment of the invention.

FIG. 9 is a block diagram of a transmission/reception circuit of the ultrasonic diagnostic equipment in the ninth embodiment of the invention. In FIG. 9, the memory 18 is a memory for storing the first receiver signal. The adder 19 is a means for adding the first and the second receiver signals. A general construction of the ultrasonic diagnostic equipment in the ninth embodiment is similar to of the ultrasonic diagnostic equipment in the first embodiment shown in FIG. 1, except that the memory 18 and the adder 19 are added on the output side of the beam forming device. FIG. 10 is an operational explanation drawing of the ultrasonic diagnostic equipment in the ninth embodiment.

Operation of the ultrasonic diagnostic equipment in the ninth embodiment of the invention constructed above will be hereinafter described. An aperture using 16 transducer elements among 32 transducer elements of the probe 1 is set as Apertures K1 to K4 in FIG. 10. The aperture is divided into two portions, and transmission and reception of ultrasonic wave is performed two times respectively. In the first time, as shown as 1A of Aperture K1 in FIG. 10, ultrasonic wave is transmitted by using eight transducer elements at the central part of the aperture. In the second time, as shown as 1B of Aperture K1 in FIG. 10, transmission is performed by using eight transducer elements at the both ends of the aperture references 2A, 2B, 3A, 3B, 4A and 4B in FIG. 10 are used for apertures K2, K3 and K4 in a similar manner as the above-mentioned references 1A and 1B. Receiver signal of the first time is stored in the memory 18. The receiver signal of the first time is outputted from the memory 18, correspondingly to a timing when a receiver signal of the second time is output from the beam forming device. These two signals are added at the adder 19. A center of Aperture K1 having an aperture width 16 pcs (in expressing by the number of the transducer elements to be used) becomes Aperture position #1. Regarding Aperture K2, a width is 16 and a center becomes Aperture position #2. Regarding Aperture K3, a width is 16 and a center becomes Aperture position #3. Regarding Aperture K4, a width of the aperture is 16 pcs (in expressing by the number of transducer elements to be used) and a center becomes Aperture position #4. By performing aperture synthesis as above, performing transmission and reception one time can provide effects similar to in performing transmission and reception with an aperture by twice of the number of channels of the transmission drive circuits.

As mentioned above, in the ninth embodiment of the invention, the ultrasonic diagnostic equipment has a construction, wherein the memory and the adder are added on the output side of the beam forming device. Therefore, a transmission circuit amount can be reduced, and an inexpensive ultrasonic diagnostic equipment can be realized while performance is maintained.

Tenth Embodiment

A tenth embodiment of the invention is an ultrasonic diagnostic equipment, wherein high voltage switches for connecting adjacent transducer elements are added.

Figure 11:
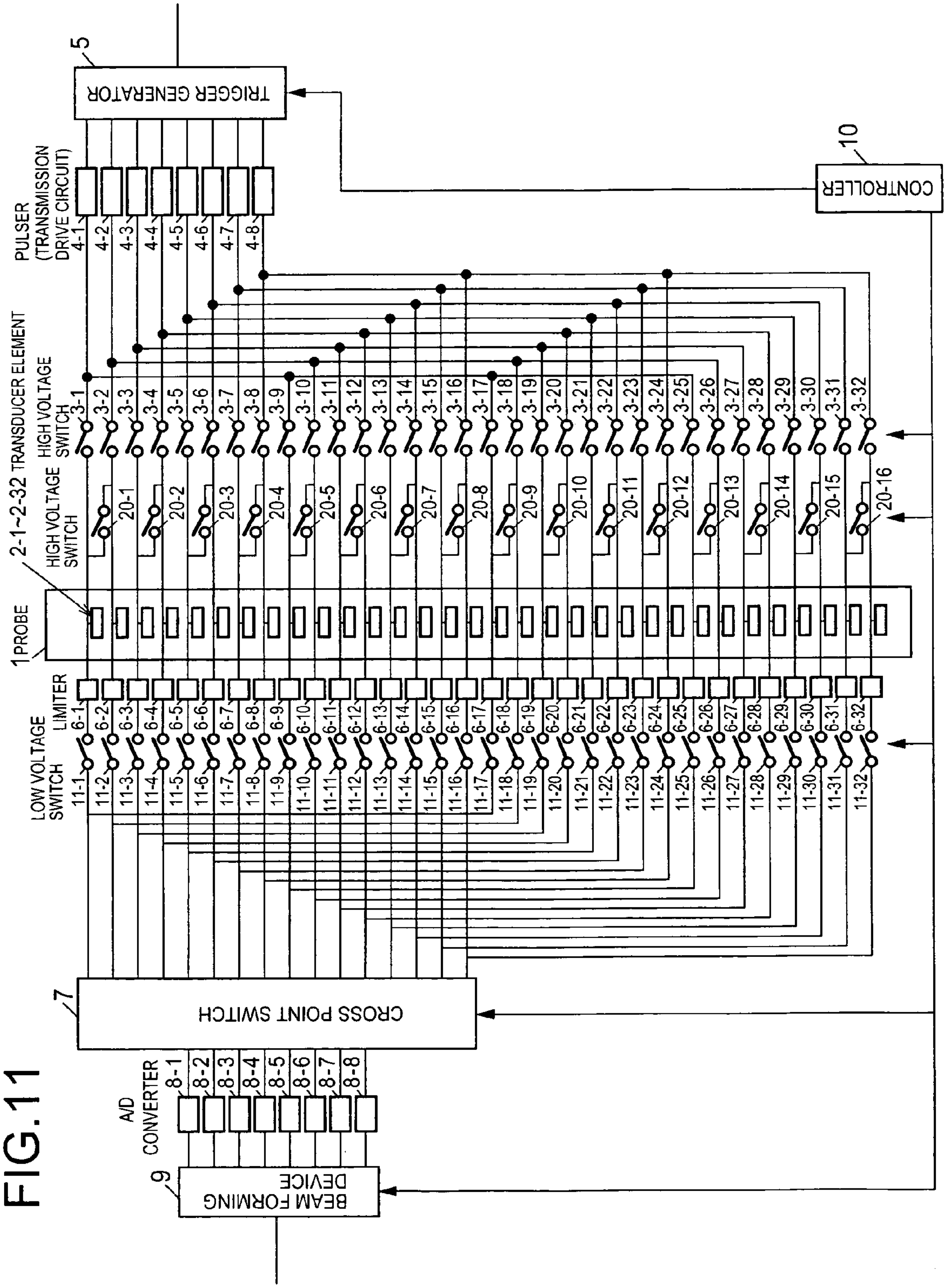
FIG. 11 is a block diagram of a front end part of an ultrasonic diagnostic equipment in a tenth embodiment of the invention.

FIG. 11 is a block diagram of a transmission/reception circuit of the ultrasonic diagnostic equipment in the tenth embodiment of the invention. In FIG. 11, high voltage switches 20-1 to 20-16 are switches for connecting adjacent transducer elements. A general construction of the ultrasonic diagnostic equipment in the tenth embodiment is similar to of the ultrasonic diagnostic equipment in the first embodiment shown in FIG. 1, except that the high voltage switches 20-1 to 20-16 for connecting adjacent transducer elements are added.

Operation of the ultrasonic diagnostic equipment in the tenth embodiment of the invention constructed above will be hereinafter described. When an aperture diameter of ultrasonic beam is widened by the method described in the second embodiment, transducer elements not driven exist between transducer elements driven. Therefore, a sound pressure is lowered where the transducer elements not driven exist. In this embodiment, in order to prevent the transducer elements not driven from existing when an aperture is widened, adjacent transducer elements are connected by the high voltage switches. A transducer element which has not been driven in the second embodiment is driven at the same timing as of the adjacent transducer element to be driven. In result, lowering a sound pressure is prevented.

Descriptions will be hereinafter given with the example of PA1 of Aperture K2 shown in FIG. 2. The transducer element 2-8 has not been driven yet. Therefore, the high voltage switch 20-4 is turned ON, and the transducer element 2-8 is also driven by high voltage transmission pulse for driving the transducer element 2-7. The transducer elements 2-10, 2-15, and 2-17 have not been driven yet as well. Therefore, the high voltage switches 20-5, 20-8, and 20-9 are turned ON, and the transducer elements 2-10, 2-15, and 2-17 are also driven by high voltage transmission pulse for driving the transducer elements 2-9, 2-16, and 2-18.

As mentioned above, in the tenth embodiment of the invention, the ultrasonic diagnostic device has a construction, wherein the high voltage switches for connecting adjacent transducer elements are added. Therefore, lowering of a sound pressure can be prevented when an aperture is widened, a transmission circuit amount can be reduced, and an inexpensive ultrasonic diagnostic equipment can be realized while performance is maintained.

Eleventh Embodiment

An eleventh embodiment of the invention is an ultrasonic diagnostic equipment, wherein diodes are inserted between transducer elements and high voltage switches.

Figure 12:
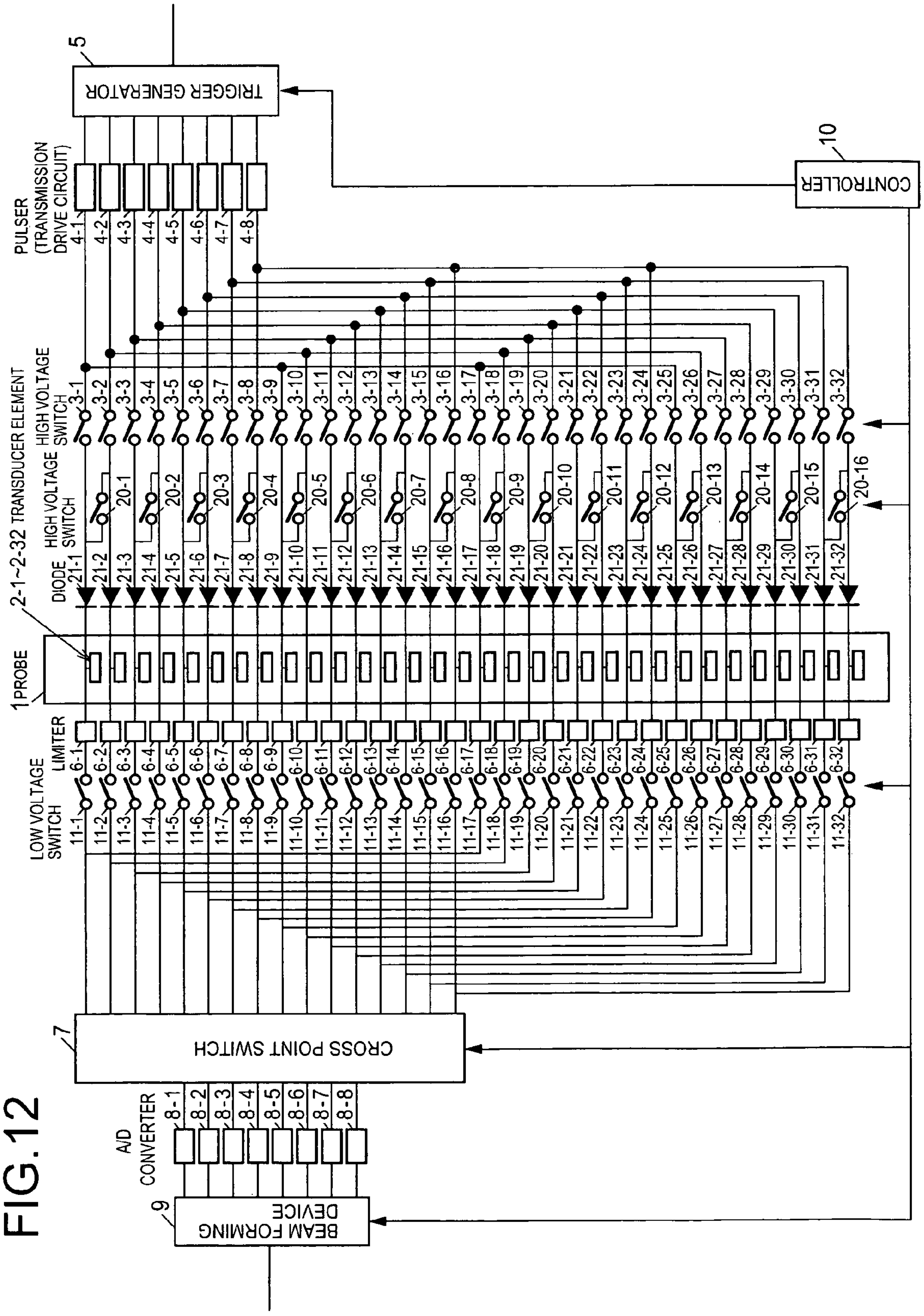
FIG. 12 is a block diagram of a front end part of an ultrasonic diagnostic equipment in an eleventh embodiment of the invention.
Figure 13:
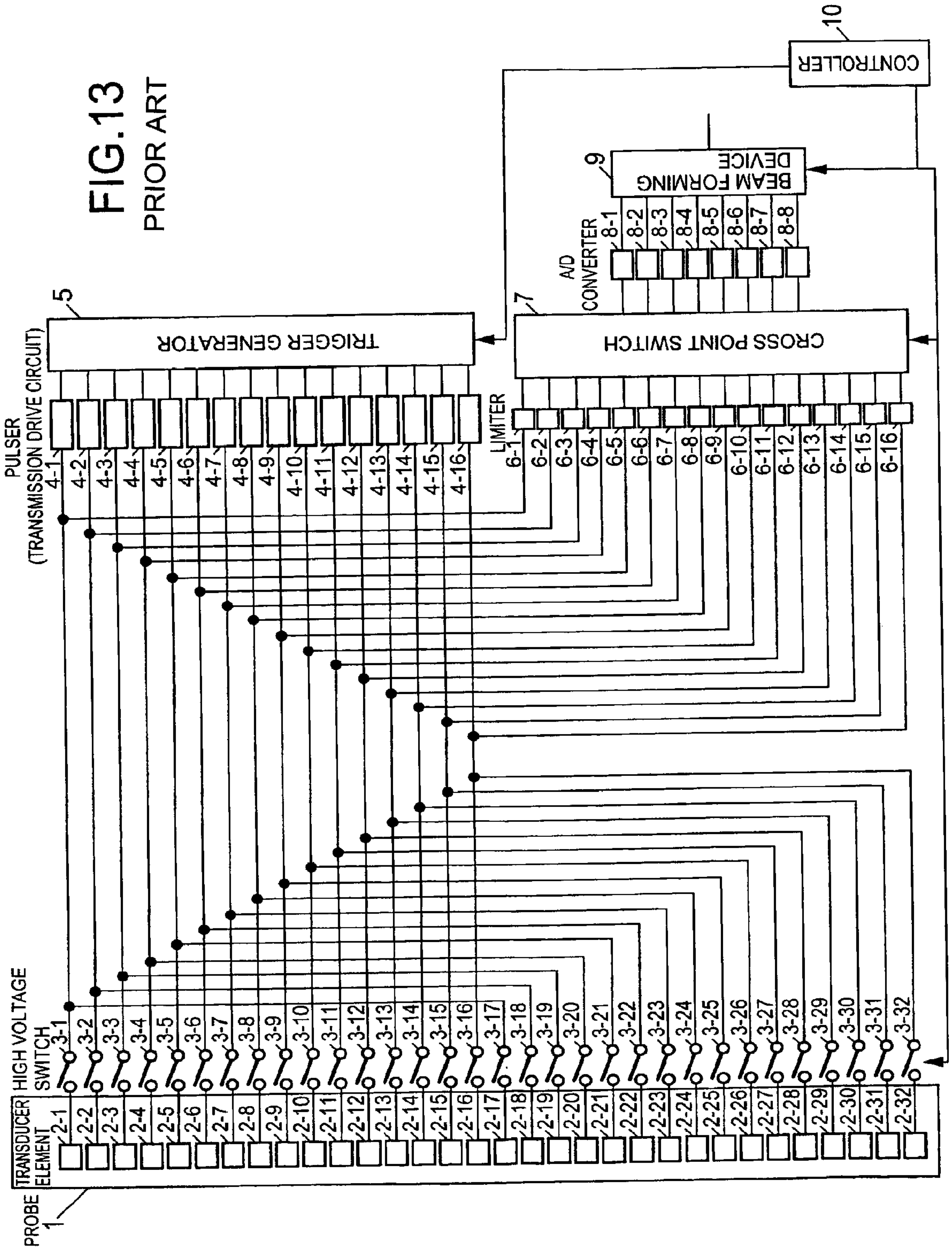
FIG.13 PRIOR ART
FIG. 13 is a block diagram of a front end part of a conventional ultrasonic diagnostic equipment.

FIG. 12 is a block diagram of a transmission/reception circuit of the ultrasonic diagnostic equipment in the eleventh embodiment of the invention. In FIG. 12, diodes 21-1 to 21-32 are. diodes for separating receiver signals for the transducer elements 2-1 to 2-32 from each other. A general construction of the ultrasonic diagnostic equipment in the eleventh embodiment is similar to of the ultrasonic diagnostic equipment in the tenth embodiment shown in FIG. 11, except that the diodes 21-1 to 21-32 are connected in series between the transducer elements and the high voltage switches.

Operation of the ultrasonic diagnostic equipment in the eleventh embodiment of the invention constructed above will be hereinafter described. In the tenth embodiment, when the adjacent transducer elements are connected, there receiver signals become the same. In order to prevent this, high voltage transmission pulse is applied to the transducer elements through the diodes 21-1 to 21-32. In the case of receiver signals having a relatively small amplitude, the diodes 21-1 to 21-32 are tuned OFF, and individuality of reception channels is maintained. Therefore, deterioration of reception beam can be prevented.

As mentioned above, in the eleventh embodiment of the invention, the ultrasonic diagnostic device has a construction, wherein the diodes are inserted between the transducer elements and the high voltage switches. Therefore, deterioration of reception beam can be prevented, a transmission circuit amount can be reduced, and an inexpensive ultrasonic diagnostic equipment can be realized while performance is maintained.

INDUSTRIAL APPLICABILITY

As evidenced by the foregoing descriptions, in the invention, high voltage switches for selectively connecting ultrasonic transducer elements and transmission drive circuits of an ultrasonic diagnostic equipment, and low voltage switches for selecting ultrasonic transducer elements which receive ultrasonic echo are provided individually. Therefore, by respectively changing connection patterns of the high voltage switches for transmission and connection patterns of the low voltage switches for reception, the following effects can be obtained. That is, even when the number of the transmission drive circuits is reduced, linear scanning can be performed without lowering precision, and an ultrasonic diagnostic equipment having a small circuit scale can be realized at low cost.

The invention claimed is:

1. An ultrasonic diagnostic equipment comprising;

a probe having a plurality of arrayed ultrasonic transducer elements, a plurality of transmission drive circuits for driving the ultrasonic transducer elements, a plurality of high voltage switches for connecting the ultrasonic transducer elements to the transmission drive circuits, a plurality of limiters for clipping transmission pulses having a given voltage or more, which are generated at the transmission drive circuits, a cross point switch having input terminals whose number is larger than the number of the transmission drive circuits for sorting and adding input signals, said cross point switch having output terminals whose number is one half of the number of said input terminals for outputting signals produced by said adding of said input signals, low voltage switches for selectively supplying output signals of the limiters to the input terminals of the cross point switch as said input signals, terminals of pairs of said low voltage switches being connected to each other in such a manner that the number of said input signals to said cross point switch becomes one half of the number of the low voltage switches, A/D converters for converting output signals of the cross point switch to digital signals, a beam forming device for delay-adding the output signals of the A/D converters, and a controller for controlling said high voltage switches and said low voltage switches in such a manner that a maximum number of said ultrasonic transducer elements which can be connected to said cross point switch is greater than a maximum number of said ultrasonic transducer elements which can be connected to said transmission drive circuits when performing one transmission and a corresponding reception.

2. The ultrasonic diagnostic equipment according to claim 1, further comprising;

a means for changing connection patterns of the high voltage switches, and a means for turning ON/OFF the high voltage switches by a connection pattern so that an aperture wider than a minimum aperture determined by the number of the transmission drive circuits is obtained.

3. The ultrasonic diagnostic equipment according to claim 2, further comprising;

a means for identifying a type of the probe, and a means for changing a size of the first-mentioned aperture according to the type of the probe.

4. The ultrasonic diagnostic equipment according to claim 2, further comprising;

a means for inputting a displayed depth, and a means for changing a size of the first-mentioned aperture according to the input displayed depth.

5. The ultrasonic diagnostic equipment according to claim 2, further comprising;

a means for inputting a display mode, and a means for changing a size of the first-mentioned aperture according to the input display mode.

6. The ultrasonic diagnostic equipment according to claim 2, further comprising;

a means for inputting a transmission focus depth, and a means for changing a size of the first-mentioned aperture according to the input transmission focus depth.

7. The ultrasonic diagnostic equipment according to claim 2, further comprising;

a means for inputting a center frequency of transmission pulse, and a means for changing a size of the first-mentioned aperture according to the input center frequency.

8. The ultrasonic diagnostic equipment according to claim 2, further comprising;

a means for selecting whether a higher resolution is prioritized or whether a wider dynamic range is prioritized, and a means for selecting transducer elements to be used according to characteristics to be prioritized.

9. The ultrasonic diagnostic equipment according to claim 2, further comprising high voltage switches, each of which connecting two adjacent transducer elements.

10. The ultrasonic diagnostic equipment according to claim 9, further comprising diodes inserted between the high voltage switches and the transducer elements.

11. The ultrasonic diagnostic equipment according to claim 1, wherein a memory for storing data related to an ultrasonic signal, and an adder for adding an output of the memory and an output of the beam forming device are provided on the output side of the beam forming device.

* * * * *